US00PP17874P3

(12) United States Plant Patent

Zaiger et al.

(10) Patent No.: US PP17,874 P3

(45) Date of Patent: Jul. 17, 2007

(54) PEACH TREE 'SUPER ZEE'

(50) Latin Name: *Prunus persica*
Varietal Denomination: Super Zee

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 13 days.

(21) Appl. No.: 11/299,550

(22) Filed: Dec. 13, 2005

(65) Prior Publication Data

US 2007/0136904 P1 Jun. 14, 2007

(51) Int. Cl.
*A01H 5/00* (2006.01)

(52) U.S. Cl. ..... Plt./197

(58) Field of Classification Search ..... Plt./197
See application file for complete search history.

*Primary Examiner*—Kent Bell
*Assistant Examiner*—Louanne Krawczewicz Myers

(57) ABSTRACT

A new and distinct variety of peach tree (*Prunus persica*). The following features of the tree and its fruit are characterized with the tree budded on 'Nemaguard' Rootstock (non-patented), grown on Hanford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit ripening in the very early maturity season.
2. Fruit with an attractive red skin color.
3. Having a low winter chilling requirement of approximately 150 to 200 hours at or below 45° F.
4. Vigorous, upright growth of the tree.
5. A productive and regular bearer of medium size fruit.
6. Fruit with good flavor and eating quality.

1 Drawing Sheet

Botanical classification: *Prunus persica.*

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree (*Prunus persica*) was originated and asexually reproduced by us in our experimental orchard located near Modesto, Stanislaus County, Calif.

PRIOR VARIETIES

Among the existing varieties of peach trees, which are known to us, and mentioned herein, 'Desert Gold' Peach (non-patented) and 'Snow Angel' Peach (application Ser. No. 10/355,917).

ORIGIN OF THE VARIETY

The new and distinct variety of peach tree (*Prunus persica*) was developed by us in our experimental orchard located near Modesto, Calif. as an open pollinated peach seedling from seed collected from our proprietary seedling '61ZB9'. The proprietary seedling (61ZB9) originated as an open pollinated seedling from seed of 'Snow Angel' Peach (application Ser. No. 10/355,917). A large number of these open pollinated peach seedlings were grown and budded to older 'Nemaguard' Rootstock (non-patented) to accelerate rapid fruit production for evaluation. Under close and careful evaluation we recognized the desirable fruit characteristics of the present early maturing variety and selected it in 2002 for further asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of peach tree (*Prunus persica*) is of large size, upright in growth and a productive and regular bearer of medium size, firm, yellow flesh fruit with good flavor and eating quality. The fruit is further characterized by ripening in the very early maturity season, having an attractive red skin color, the flesh being moderately juicy with a mild acid flavor. The tree having a low winter chilling requirement of approximately 150 to 200 hours at or below 45° F. In comparison to the low winter chilling variety 'Desert Gold' Peach (non-patented), has a lower chilling requirement of approximately 150 hours, has fruit with firmer flesh, larger in size and is approximately 30 days earlier in maturity. In comparison to its grandparent 'Snow Angel' Peach (Plant patent application Ser. No. 10/355,917), the new variety is approximately 14 days earlier in maturity and has yellow flesh compared to white flesh.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, 5 years of age, its flowers, foliage and fruit, as based on observations of a 5 year old specimen grown near Modesto, Calif., with color in accordance with Munsell Book of Color.

Tree:

*Size.*—Large. Normal for most varieties of peach trees. Pruned to 3 to 3.5 meters in height for economical harvesting of fruit. Average spread 3 meters. Average height 3.5 meters, varies with different cultural practices.

*Vigor.*—Vigorous, growth of 1.5 to 2 meters in height the first growing season. Varies slightly with fertility, type of soil and cultural practices.

*Form.*—Upright, usually pruned to vase shape.

*Branching habit.*—Upright, crotch angle approximately 35°, increases with heavy crop load.

*Productivity.*—Productive. Normal fruit thinning and spacing necessary for desirable market size fruit. Fruit set varies with climatic conditions at bloom time.

*Bearer.*—Regular, adequate fruit set 3 consecutive years. No alternate bearing observed.

*Fertility.*—Self fertile.

*Density.*—Medium dense. Pruning to vase shape desirable for sunlight penetration to enhance fruit color and keep fruit wood healthy.

*Hardiness.*—Hardy in all stone fruit growing areas of California. Winter chilling requirement approximately 150 to 200 hours at or below 45° F.

Trunk:

*Size.*—Large. Average circumference 58.4 cm at 20.4 cm above ground on a 5 year old tree.

*Stocky.*—Medium.

*Texture.*—Medium shaggy, roughness increases with age of tree.

*Color.*—Varies from 10YR 3/4 to 2.5Y 6/2.

Branches:

*Size.*—Medium. Average lateral branch length 2 to 2.5 feet. Average circumference 21.7 cm at 1.2 meters above ground. Crotch angle approximately 35°, increases with heavy crop load.

*Surface texture.*—New growth relatively smooth. Mature growth medium rough.

*Lenticels.*—Average number 29 in a 25.8 square cm area. Average length 3.2 mm. Average width 2.0 mm. Color varies from 7.5YR 5/8 to 10YR 6/8.

*Color.*—New growth varies from 2/5GY 6/6 to 2.5GY 5/6. Mature growth varies from 2.5YR 4/4 to 2.5YR 3/4, varies with age of growth.

Leaves:

*Size.*—Medium to large. Average length 124.5 mm. Average width 30.9 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slightly indented over midrib and leaf veins, glabrous. Lower surface relatively smooth, small ridges created by midrib and pinnate venation, glabrous.

*Petiole.*—Medium. Average length 9.6 mm. Average width 1.2 mm. Longitudinally grooved. Both upper and lower surfaces glabrous. Color varies from 2.5GY 7/8 to 2.5GY 6/8.

*Glands.*—Type — globose. Small. Average length 0.6 mm. Average diameter 0.3 mm. Average number 1, varies from 1 to 2. Located primarily on base of leaf blade and upper portion of petiole. Color varies from 5GY 6/6 to 7.5GY 4/2.

*Color.*—Upper surface varies from 5GY 4/4 to 5GY 3/4. Lower surface varies from 5GY 5/4 to 5GY 4/4. Midvein color varies from 2.5Y 8/4 to 2.5Y 8.5/4.

*Venation.*—Pinnately veined.

Flower buds:

*Size.*—Large. Average length 16.4 mm. Average diameter 10.2 mm.

*Hardiness.*—Hardy in all stone fruit growing areas of California. Grown in USDA Hardiness Zone 9.

*Form.*—Conical, becoming elongated just before opening.

*Pedicel.*—Average length 3.6 mm. Average width 1.0 mm. Color varies from 2.5GY 6/6 to 5GY 6/6.

*Color.*—Varies from 7.5RP 6/12 to 5RP 8/6.

Flowers:

*Size.*—Large, showy. Average height 18.8 mm. Average diameter 29.5 mm.

*Petals.*—Number 5, alternatively arranged to sepals. Size — large. Average length 17.3 mm. Average width 17.6 mm. Form — orbicular. Margin — sinuate, slightly cupped. Color both upper and lower surfaces varies from 5RP 7/8 to 5RP 8/6, fades with age of flower.

*Sepals.*—Number 5, alternately arranged to petals. Size — medium. Average length 5.4 mm. Average width 5.1 mm. Shape — ovate, apex rounded. Margin — entire. Color — lower surface varies from 5GY 6/6 to 5R 3/4, pubescent. Upper surface varies from 5GY 6/6 to 5GY, glabrous.

*Stamens.*—Average number per flower — 44. Average filament length 14.0 mm. Filament color varies from N 9.5/ (white) to 2.5RP 9/2. Anther color varies from 5R 4/10 to 7.5R 4/10.

*Pollen.*—Self fertile. Color varies from 2.5Y 7/8 to 2.5Y 7/10.

*Pistil.*—Normally one. Surface — pubescent. Average length 16.9 mm. Position of the stigma even in height with anthers. Color varies from 2.5GY 9/6 to 2.5GY 8/6.

*Fragrance.*—Slight.

*Blooming period.*—Date of First Bloom Jan. 28, 2005. Date of Petal Fall Feb. 10, 2005, varies slightly with climatic conditions.

*Color.*—Varies from 7.5RP 7/8 to 5RP 8/6.

*Number flowers per flower bud.*—One.

*Pedicel.*—Average length 4.5 mm. Average width 1.0 mm. Color varies from 5GY 6/6 to 5GY 5/6.

Fruit:

*Maturity when described.*—Firm ripe.

*Date of first picking.*—Apr. 26, 2005.

*Date of last picking.*—May 2, 2005, varies slightly with climatic conditions.

*Size.*—Medium. Average diameter axially 56.7 mm. Average transversely in suture plane 60.9 mm. Average weight 119.3 grams, varies slightly with fertility of the soil, amount of thinning and climatic conditions.

*Form.*—Globose.

*Suture.*—Nearly smooth, extends from base to apex.

*Ventral surface.*—Nearly smooth.

*Apex.*—Varies from slight tip to slightly retuse.

*Base.*—Flat to slightly retuse.

*Cavity.*—Rounded to slightly elongated in suture plane. Average depth 3.3 mm. Average diameter 12.5 mm.

Stem:

*Size.*—Medium. Average length 8.6 mm. Average diameter 2.7 mm.

*Color.*—Varies from 2.5GY 6/8 to 2.5GY 5/8.

Flesh:

*Ripens.*—Evenly.

*Firmness.*—Firm, firmer than most early maturing standard varieties.

*Fibers.*—Few, small, tender.

*Texture.*—Firm, holds firm well for very early maturing variety.

*Aroma.*—Moderate.

*Amydgalin.*—Undetected.

*Eating quality.*—Good.

*Flavor.*—Good.

*Juice.*—Moderate, enhances flavor.

*Brix.*—Average Brix 9.6°, varies slightly with amount of fruit per tree and climatic conditions.

*Color.*—Varies from 2.5Y 8/8 to 5Y 8/8. Pit cavity varies from 2.5Y 6/8 to 2.5Y 6/10.

Skin:

*Thickness.*—Medium.

*Surface.*—Smooth.

*Down.*—Pubescent, moderate amount.

*Tendency to crack.*—None.

*Color.*—Ground color varies from 5Y 9/4 to 7.5Y 9/4. Nearly overspread with 5R 4/10 to 7.5R 4/8.

*Tenacity.*—Tenacious to flesh.

*Astringency.*—None.

Stone:

*Type.*—Clingstone.

*Size.*—Large. Average length 30 mm. Average width 24.1 mm. Average thickness 21.1 mm.

*Form.*—Ovoid.

*Base.*—Usually flat, varies from flat to rounded.

*Apex.*—Pointed. Average length of point 0.3 mm.

*Surface.*—Pitted throughout, pits vary from rounded to elongated. Stone surface not as hard as later maturing varieties.

*Sides.*—Unequal, one side slightly larger, extending further from suture plane.

*Ridges.*—Relatively smooth with wide surface, extending from base toward apex.

*Tendency to split.*—Slight to moderate internal stone splits.

*Color.*—Varies from 7.5YR 7/8 to 7.5YR 6/8.

Kernal:

*Form.*—Ovate.

*Viability.*—Poor, embryo only partially developed.

*Size.*—Medium to large. Average length 16.4 mm. Average width 9.5 mm. Average depth 4.3 mm.

*Skin.*—Color varies from 2.5Y 9/2 to 5Y 8.5/2.

Use: Dessert. Market — local and long distance.

Keeping quality: Good, held firm in cold storage at 38° to 42° F. for 2 weeks without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of peach tree, substantially as illustrated and described, characterized by its large size, vigorous, upright growth and a productive and regular bearer of medium size fruit with good flavor and eating quality; the fruit is further characterized with maturing in the very early season, the tree having a low winter chilling requirement of approximately 150 to 200 hours at or below 45° F. and in comparison to 'Snow Angel' Peach (Plant patent application Ser. No. 10/355,917), the new variety is approximately 14 days earlier in maturity and has yellow flesh compared to white flesh.

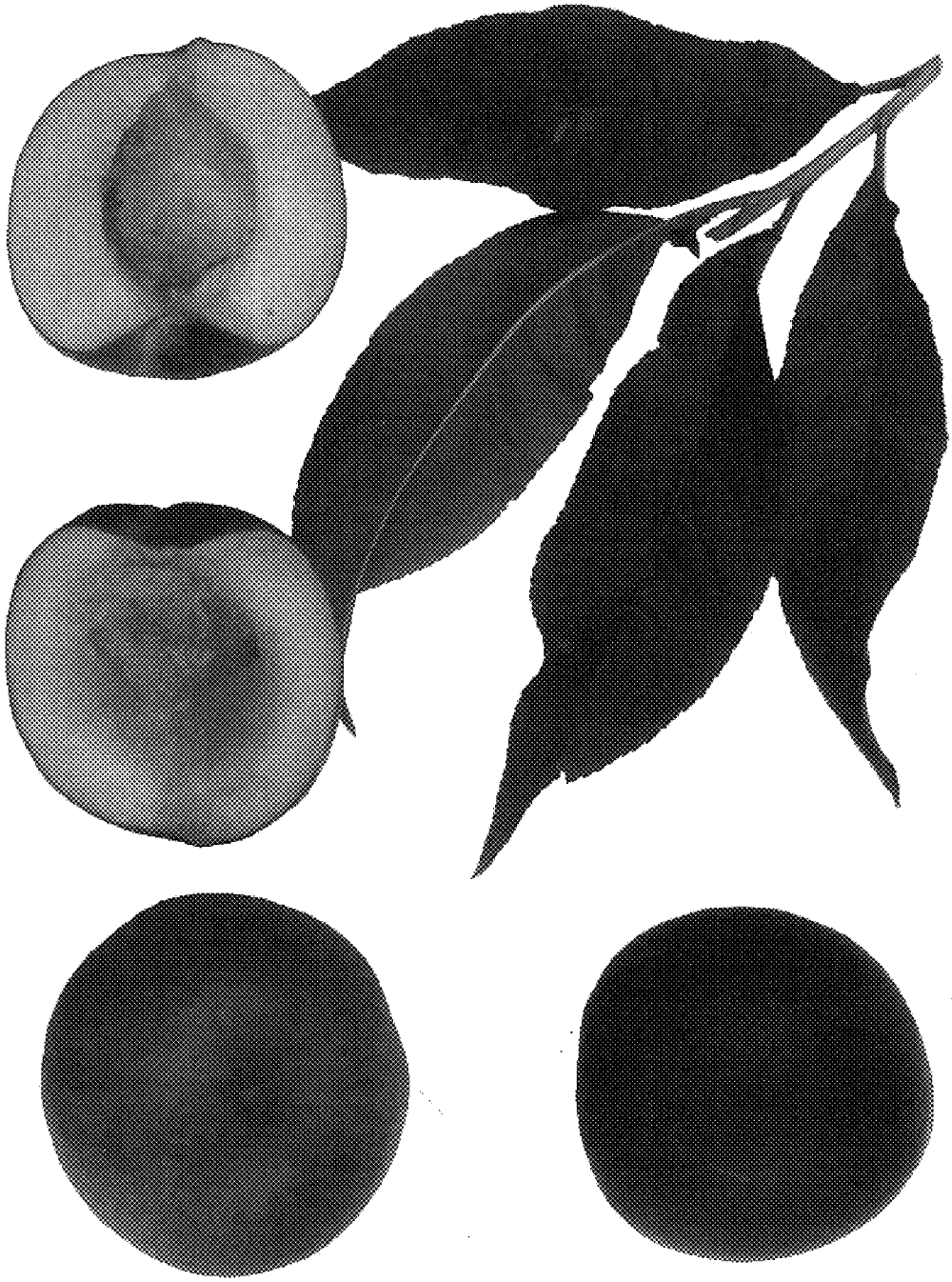

* * * * *